United States Patent [19]

Lassen

[11] Patent Number: 4,745,122

[45] Date of Patent: May 17, 1988

[54] METHOD FOR TREATING OBESITY

[75] Inventor: Joergen B. Lassen, Glostrup, Denmark

[73] Assignee: A/S Ferrosan, Soberg, Denmark

[21] Appl. No.: 804,810

[22] Filed: Dec. 4, 1985

[30] Foreign Application Priority Data

Dec. 4, 1984 [GB] United Kingdom ............... 8430581

[51] Int. Cl.[4] .............................................. A61K 31/435
[52] U.S. Cl. .................................... 514/321; 514/909
[58] Field of Search ............................. 514/321, 909

[56] References Cited

U.S. PATENT DOCUMENTS 3,982,001 9/1976 Heffe et al. ......................... 514/321
4,007,196 2/1977 Christensen et al. ............... 546/197
4,442,113 4/1984 Lassen et al. ....................... 514/910

OTHER PUBLICATIONS

Chem. Abst. 90:66758t (1979)–Petersen et al.
Chem. Abst. 91:32625c (1979)–Lund et al.
Chem. Abst. 98:46683(b) (1983)–Lund et al.
Chem. Abst. 98:101116w (1983)–Magnussen et al.
Chem. Abst. 98:172969n (1983)–Borup et al.

*Primary Examiner*—Douglas W. Robinson
*Attorney, Agent, or Firm*—Hopgood, Calimafde, Kalil, Blaustein & Judlowe

[57] ABSTRACT

A method for treating obesity in humans or non-human animals, which method comprises administering an effective, non-toxic amount of paroxetine or a pharmaceutically acceptable salt thereof, to obese humans or animals and compositions for use in such treatment.

15 Claims, No Drawings

METHOD FOR TREATING OBESITY

The present invention relates to a method for the treatment of obesity and to a compound for use in such method.

U.S. Pat. No. 4,007,196 discloses the compound, (−)-trans-4-(4'-fluorophenyl)-3-(3',4'-methylenedioxyphenoxymethyl)piperidine, and, in Example 2, a process by which it can be prepared. The compound, which is referred to herein by its common name, paroxetine, is described in the patent as an inhibitor of 5-hydroxytryptamine and, therefore, is of use in the treatment of depression. The patent also mentions that paroxetine is useful in the treatment of Parkinson's disease.

It has now been discovered that paroxetine also has activity against obesity.

Accordingly, the present invention provides a method for treating obesity in human or non-human animals, which method comprises administering an effective, non-toxic amount of paroxetine or a pharmaceutically acceptable salt thereof, to obese humans or non-human animals.

The administration to the human or animal may be by way of oral administration or parenteral administration. An effective amount of paroxetine or a pharmaceutically acceptable salt thereof may be determined in accordance with the usual factors such as the severity of the condition and the weight of the human or animal requiring treatment. However it is believed that an amount of from 0.01 to 100 mg/kg per day should be sufficient for effective treatment; suitably an amount of from 0.1 to 50 mg/kg, and favorably, especially for humans, an amount of from 0.1 to 20 mg/kg, preferably 0.1 to 5 mg/kg, such as 0.1 to 1 mg/kg.

Suitably, the invention provides a method for treating obesity in human or non-human mammals.

It is preferred that paroxetine or a pharmaceutically acceptable salt thereof is administered in the form of a unit-dose pharmaceutical composition in which it is combined with a pharmaceutically acceptable carrier; such as a unit-dose oral or parenteral composition.

Examples of oral compositions include tablets and capsules which generally contain conventional excipients, such as a binding agent, filler, lubricant, and disintegrating agent. An oral composition may also be in the form of a liquid, such as an aqueous or oily suspension, a solution, emulsion, syrup or elixir, or it may be in the form of a dry product for reconstitution with water or any other pharmaceutically acceptable liquid vehicle. Such liquid compositions generally contain conventional additives where appropriate, such as a suspending agent, emulsifying agent, preservative or flavouring agent.

Examples of parenteral compositions include suspensions and solutions which generally contain a surfactant or wetting agent and one or more adjuvants, such as a local anaesthetic, preservative or buffering agent. A parenteral solution may be prepared by dissolving paroxetine or a pharmaceutically acceptable salt thereof in an aqueous or non-aqueous vehicle and filter sterilizing it prior to filling into a vial or ampoule and sealing. A parenteral suspension may be prepared in much the same manner except that paroxetine or the pharmaceutically acceptable salt thereof is suspended, rather than dissolved, in the vehicle and that sterilization is carried out prior to suspension by exposure of the compound or salt to ethylene oxide.

A unit-dose composition, preferably, contains from 0.1 to 100 mg, such as 0.5 to 50 mg of paroxetine or a pharmaceutically acceptable salt thereof. Such unit-dose compositions may be administered from one to six times per day such that the total daily dose is in the range mentioned hereinbefore for effective treatment.

As used herein the terms 'pharmaceutical composition' and 'pharmaceutically acceptable' embrace compositions and ingredients for both human and veterinary use.

Examples of a pharmaceutically acceptable salt of paroxetine include paroxetine hydrochloride, paroxetine hydrobromide, paroxetine acetate and paroxetine maleate.

The present invention also provides paroxetine or a pharmaceutically acceptable salt thereof for use in the treatment of obesity. Such treatment may be carried out in the manner as described hereinbefore.

The present invention further provides a pharmaceutical composition for use in the treatment of obesity, which comprises an effective non-toxic amount of paroxetine or a pharmaceutically acceptable salt thereof and a pharmaceutically acceptable carrier. Such composition may be prepared in the manner as described hereinbefore.

The following pharmacological data illustrates the invention.

METHODS

Forty female Sprague-Dawley rats were housed in pairs and fed on Oxoid pelleted diet. Eight rats were allocated to each of two treatment groups.

1. Controls, fed ad libitum (Group 1).
2. Paroxetine HCl 50 mg/kg p.o., daily (Group 2)

The rats were dosed between 11.00 and 13.00 h; the control animals were given water.

Food intake was measured daily, body weight was measured on days 1, 8, 14 and 23 (termination day).

Perirenal and parametrial fat pad weights were measured at the end of the study to provide an indication of the lipid content of the rats.

Statistical significance was assessed by analysis of variance in conjunction with Student's 't'-test. The results are shown in Table 1.

TABLE 1

Effects of Paroxetine in 22-day Dose Study
Results are means ± S.E.M. of 8 (weight gain and fat pad weights) or 4 (food intake) results.

| Test Parameter | Test Time Period | Group 1 Controls | Group 2 Paroxetine |
|---|---|---|---|
| Wt. at start (g) | | 131 ± 2 | 132 ± 2 |
| Wt. gain | Days 1–8 | 43.1 ± 1.5 | 21.6 ± 3.3*** |
| | Days 1–14 | 63.5 ± 1.7 | 37.0 ± 4.7*** |
| | Days 1–23 | 94.1 ± 3.4 | 59.3 ± 6.6*** |
| Food intake (g/rat) | Days 1–8 | 123 ± 2 | 92 ± 7*** |
| | Days 1–14 | 237 ± 2 | 186 ± 7*** |
| | Days 1–23 | 438 ± 4 | 334 ± 14*** |
| Fat pad wt. (g) | Parametrial | 2.02 ± 0.17 | 1.28 ± 0.17* |
| | Perirenal | 2.61 ± 0.13 | 1.47 ± 0.27*** |

*$P<0.05$,
**$P<0.01$,
***$P<0.001$

TOXICITY

Oral $LD_{50}$ values for rat and mice were 374 mg/kg and 341 mg/kg respectively, dosages being expressed in terms of paroxetine pure free base.

I claim:

1. A method for treating obesity in human or non-human animals, which method comprises administering an anti-obesity effective, non-toxic amount of paroxetine or a pharmaceutically acceptable salt thereof, to obese humans or non-human animals.

2. A method according to claim 1, which method comprises the administration of paroxetine or a pharmaceutically acceptable salt thereof by way of oral administration or parenteral administration.

3. A method according to claim 1, which method comprises the administration of from 0.01 to 100 mg/kg per day of paroxetine or a pharmaceutically acceptable salt thereof.

4. A method, according to claim 3, which method comprises the administration of from 0.1 to 50 mg/kg per day.

5. A method, according to claim 1, which method comprises the administration of paroxetine.

6. A method, according to claim 1, which method comprises the administration of a pharmaceutically acceptable salt of paroxetine.

7. A method according to claim 6, wherein the pharmaceutically acceptable salt is that selected from the group consisting of: paroxetine hydrochloride, paroxetine hydrobromide, paroxetine acetate and paroxetine maleate.

8. A method according to claim 1, wherein the pharmaceutically acceptable salt is paroxetine hydrochloride.

9. A method for treating obesity in human or non-human animals, which method comprises the administration of an anti-obesity effective, non-toxic amount of a pharmaceutical composition, which composition comprises an effective non-toxic amount of paroxetine or a pharmaceutically acceptable salt thereof and a pharmaceutically acceptable carrier therefor.

10. A method according to claim 9, wherein the composition is a unit dose composition.

11. A method, according to claim 10, wherein a unit dose contains from 0.1 to 100 mg of paroxetine or a pharmaceutically acceptable salt thereof.

12. A method, according to claim 10, wherein a unit dose contains from 0.5 to 50 mg of paroxetine or a pharmaceutically acceptable salt thereof.

13. A method, according to claim 9, wherein the composition comprises paroxetine.

14. A method, according to claim 9, wherein the composition comprises a pharmaceutically acceptable salt selected from the group consisting of: paroxetine hydrochloride, paroxetine hydrobromide, paroxetine acetate and paroxetine maleate.

15. A method, as claimed in claim 9, wherein the composition comprises paroxetine hydrochloride.

* * * * *